United States Patent [19]

Perrier et al.

[11] Patent Number: 5,912,016

[45] Date of Patent: Jun. 15, 1999

[54] PARTICLES OF CROSSLINKED PLANT PROTEINS AND THE PROCESS FOR THEIR PREPARATION

[75] Inventors: Eric Perrier, Les Cotes D'Arey; Marie-Christine Levy, Reims; Patricia Lacazette, Saint André de Corcy; Chantal Buffevant, Millery, all of France

[73] Assignee: Coletica, Lyons, France

[21] Appl. No.: 08/944,047

[22] Filed: Sep. 9, 1997

[30] Foreign Application Priority Data

Jul. 15, 1997 [FR] France ................................. 97 08968

[51] Int. Cl.$^6$ ...................................................... A61K 9/14
[52] U.S. Cl. ........................ 424/489; 424/499; 424/488; 424/195.1
[58] Field of Search ..................... 424/489, 468, 424/488, 499, 195.1

[56] References Cited

U.S. PATENT DOCUMENTS 5,395,620   3/1995   Hue et al. ............................... 424/499

*Primary Examiner*—Thurman K. Page
*Assistant Examiner*—William E. Benston, Jr.
*Attorney, Agent, or Firm*—Wolf, Greenfield & Sacks P.C.

[57] ABSTRACT

The invention relates to particles. These particles comprise, at least on the surface, a wall formed of plant proteins crosslinked particularly by means of interfacial crosslinking between the plant proteins and an acylating polyfunctional crosslinking agent comprising at least two acylating groups, covalent bonds being formed between the acylatable groups of the proteins and the acyl groups of the acylating polyfunctional crosslinking agent. These particles are used for the manufacture of a cosmetic, pharmaceutical, dermatological or food composition.

48 Claims, No Drawings

PARTICLES OF CROSSLINKED PLANT PROTEINS AND THE PROCESS FOR THEIR PREPARATION

The present invention relates essentially to particles, especially microparticles or nanoparticles, of crosslinked plant proteins, to the process for their preparation and to cosmetic, pharmaceutical or food compositions in which they are present.

TECHNOLOGICAL BACKGROUND

It is well known that the encapsulation of active substances offers important advantages such as, for example, the protection of the substance or its slow or delayed release at the site of use.

For applications in the cosmetic, pharmaceutical or food sectors, the materials which are most widely sought after as constituents of the wall are natural substances, particularly proteins or polysaccharides, because of their biocompatibility.

Some microencapsulation processes using proteins or polysaccharides derive from the interfacial polycondensation method described by Chang (Chang T. M. S., Science, 1964, 146, 524–525). According to this well-known method, an aqueous solution of a diamine is emulsified in a hydrophobic phase, and a solution of a diacid chloride is then added to the emulsion. The amine groups form amide linkages with the acid dichloride at the interface to give a membrane which individualizes microcapsules. It is known that the polycondensation reaction is promoted by the alkalization of the aqueous phase since the reaction releases hydrochloric acid, which, in the absence of an alkaline agent, protonates some of the amine groups and thereby makes them non-acylatable. The same applies when the diamine is replaced with a protein in order to form microcapsules of crosslinked protein. In the processes described in the literature of the prior art, the initial aqueous solution of protein is alkalized so that all the free amine groups of the protein are in an acylatable, non-protonated form. Thus, for example, the document U.S. Pat. No. 4,780,321 in the name of LEVY relates to the preparation of microcapsules with mixed walls formed of crosslinked polysaccharides and proteins. The initial aqueous solution of polysaccharide and protein is alkaline, the pH preferably being >10. Likewise, in the document U.S. Pat. No. 5,395,620 in the name of HUC, which relates to microcapsules with a wall of crosslinked atelocollagen and glycosaminoglycans, the pH of the initial aqueous solution is preferably basic, all the Examples in said patent using a carbonate buffer of pH 9.8.

In the document FR-A-2,444,497 in the name of Mars, an aqueous solution of protein is used without the addition of alkaline substances or buffers. However, the aqueous phase contains a high concentration of protein, equal to at least 20% (w/w), so that part of it serves to neutralize the HCl formed (buffer role) while the non-protonated fraction can be used to form the membrane.

Glutaraldehyde can also be used to manufacture particles from proteins. The crosslinking is generally effected in a neutral or alkaline medium. Thus, for example, serum albumin can be crosslinked in 20% solution in a phosphate buffer of pH 7.5 (Sheu M. T. et al., J. Parenter, Sci. Technol., 1986, 40, 253–258) with 1% of glutaraldehyde. However, the mechanism of the reaction of glutaraldehyde with the proteins is complex and remains poorly elucidated. It is known that the reaction involves not only the free glutaraldehyde but also polymeric forms originating from the condensation of glutaraldehyde with itself, it being possible for these derivatives to exist in linear or cyclic form. The composition of the glutaraldehyde solutions in terms of these different reactive forms is variable and depends on diverse factors, so the nature of the bonds formed and the degree of crosslinking are not completely controlled; this is an obstacle to industrial development (Saleh A. M. et al., Int. J. Pharm., 1989, 57, 205–210). Furthermore, this very reactive crosslinking agent can interfere with various active principles and thereby reduce their bioavailability (Gupta P. K. and Hung C. T., J. Microencapsulation, 1989, 6, 427–462). Finally, free aldehyde groups can be present on the particles (Magee G. A. et al., J. Controlled Release, 1995, 37, 11–19). The presence of such reactive groups on particles intended for human use is not desirable. For example, toxic effects of empty particles have been observed on macrophages (Suunders J. et al., Int. J. Pharm., 1991, 68, 265–270).

The proteins mentioned in the documents of the literature of the prior art are animal proteins, none of them mentioning the use of plant proteins.

If the conditions described in the documents of the prior art, where the aqueous phase used to dissolve the plant proteins is a sodium carbonate buffer of pH 9.8, are applied to commercially available plant protein preparations, it is not possible to obtain stable microcapsules. The microcapsules are obtained in very small quantities. They have a fragile membrane: some of them often appear to be open under microscopic examination. They form numerous aggregates and deteriorate very rapidly in a few days at 45° C. in the form of an aqueous suspension. The same applies when phosphate buffers with a pH of between 7 and 8, or simply distilled water, are used to dissolve the plant proteins.

Similarly, stable microcapsules are not obtained if liquid preparations containing plant proteins, such as commercial soya milks, are used directly without being buffered, or if they are buffered by the addition of sodium carbonate or sodium phosphate.

SUMMARY OF THE INVENTION

Totally unexpectedly, it has been discovered that if the particles are prepared using solutions of plant proteins whose pH values are close to neutrality or even slightly acidic, i.e. in a pH range from about 4.5 to about 8, and which contain at least one carboxylic acid salt, particularly an alkali metal or alkaline earth metal salt, preferably an alkali metal salt, it is then possible to prepare stable particles, especially microparticles or nanoparticles, of crosslinked plant proteins. Such solutions of plant proteins can be obtained either by using buffer solutions containing said salts in order to extract the proteins contained in pulverulent plant protein preparations, or by adding said salts to liquid preparations containing plant proteins, such as commercial soya milks.

This result is all the more unexpected because the pH values of these solutions are relatively low and because the concentrations of dissolved proteins in the aqueous phase are low, always being less than about 5% by weight.

OBJECTS OF THE INVENTION

Thus one main object of the present invention is to solve the novel technical problem which consists in providing a solution for the preparation of stable particles, especially microparticles or nanoparticles, microcapsules or nanocapsules or microspheres or nanospleres, from plant proteins.

Another main object of the present invention is to solve the novel technical problem which consists in providing a solution for the preparation of stable particles, especially microparticles or nanoparticles, microcapsules or nanocapsules or microspheres or nanospheres, from plant proteins while at the same time optionally allowing the encapsulation of one or more active substances in the form of a solution, suspension or emulsion.

Another object of the present invention is to solve the above-mentioned novel technical problems by means of simple manufacturing processes which can be used on the industrial scale, particularly in the cosmetic, pharmaceutical or food industry. This solution should preferably make it possible to prepare particles whose size can be adjusted at will, particularly over a range of dimensions from a nanometer to a few millimeters, especially from about 10 nanometers to about 3 mm.

BRIEF DESCRIPTION OF THE INVENTION

Within the framework of the invention, particle is understood as meaning a particle of essentially spherical shape which can have either a vesicular structure or a homogeneous structure. The particles therefore include any sphere or capsule. For particles of vesicular structure, comprising a separate outer coating forming a membrane around the contents, the general term used is capsules, particularly microcapsules or nanocapsules in the case of dimensions of the order of a micrometer or nanometer respectively. For particles of monolithic homogeneous structure, the usual term used is spheres, particularly microspheres or nanospheres in the case of dimensions of the order of a micrometer or nanometer respectively. These particles together form an integral part of the present invention.

This solution should also preferably make it possible to prepare biocompatible and biodegradable particles.

Thus, according to the present invention, it has been discovered, totally unexpectedly, that stable particles can be obtained by initiating an interfacial crosslinking reaction between plant proteins and an acylating polyfunctional crosslinking agent, particularly a diacid halide, preferably a diacid chloride, at the interface of the phases of an emulsion, particularly an emulsion of the "water-in-oil" or "oil-in-water" type.

In the case of an emulsion of the "water-in-oil" type, in a first embodiment of the invention, an aqueous phase containing the plant proteins and at least one carboxylic acid salt is first emulsified in a hydrophobic phase, after which the solution of crosslinking agent is added to the emulsion. It is then found that membranes consisting of crosslinked molecules of the plant protein form at the interface of the aqueous droplets.

The particles are sufficiently stable to withstand prolonged incubation in an oven at 45° C. in the form of an aqueous suspension without their structure being destroyed.

The particles are rapidly lyzed in the presence of a protease, which demonstrates their biodegradability.

Depending on the conditions chosen for the emulsification, the particle size can vary from less than 1 micron, i.e. nanometer size, for example by using a high pressure homogenizer, to several hundred micrometers or even a millimeter or more.

It has also been discovered that it is possible to obtain large particles, especially capsules, of crosslinked plant proteins with a mean size in excess of 500 µm, it being possible for a fraction of these particles to have a diameter in excess of a millimeter. To do this, the aqueous phase containing the plant proteins and at least one carboxylic acid salt has to be dispersed in a hydrophobic phase under conditions of gentle agitation, optionally without a surfactant, to give dispersed droplets of appropriate size. The crosslinking agent is then added to form the membrane of crosslinked proteins.

It has also been discovered that the mean diameter of the particles and the proportion of particles with a size greater than a millimeter can be increased by incorporating a small amount of an insoluble lipophilic substance into the aqueous phase, into the hydrophobic phase or into both phases before the emulsification is carried out, examples of said substance being titanium oxide, zinc oxide, talcum, calcium stearate or an insoluble colorant in the form of a pigment or lake.

It has also been discovered that particles can be obtained by initiating the crosslinking reaction in an emulsion of the "oil-in-water" type. In this case, a hydrophobic phase containing a polyfunctional crosslinking agent having at least two acylating groups, preferably a diacid halide, particularly a diacid chloride, is emulsified in an aqueous phase containing plant proteins and at least one carboxylic acid salt, used as the continuous phase. The reaction is allowed to develop at the interface and agitation is maintained for an appropriate time. It is found that a membrane forms around the dispersed hydrophobic droplets to give particles with hydrophobic contents, consisting of capsules in this case.

Thus suitable solutions can be obtained from various commercially available pulverulent plant protein preparations, such as flours, concentrates or isolates, by using buffers containing, for example, sodium acetate, sodium succinate or sodium citrate. To prepare the solutions of plant proteins, a sample of the flour, concentrate or isolate is dispersed in the buffer solution and agitation is started, optionally with the assistance of heating to a moderate temperature, for example of between 30 and 50° C. After an appropriate time, generally of between 5 min and 30 min, the insoluble fraction is removed, for example by centrifugation. The supernatant, containing the plant proteins in solution in the buffer, is then used as the aqueous phase for the preparation of particles by interfacial crosslinking by means of crosslinking agents, particularly diacid halides.

Likewise, the addition of at least one alkali metal salt of a carboxylic acid, such as sodium acetate or sodium citrate, to liquid plant protein preparations, such as soya milks, gives an aqueous phase which makes it possible to obtain stable particles from these milks.

It has also been discovered that it is possible to obtain particles of crosslinked plant proteins which have a very small size of less than a micrometer, an intermediate size of the order of a micrometer, or a large size, i.e. with a diameter of around a millimeter or even in excess of a millimeter, and which have a high stability and a high mechanical strength. The mean diameter of these particles, in this case microcapsules or capsules, can exceed 500 µm and even reach 800 to 900 µm, a fraction of the particles then having a diameter in excess of a millimeter.

Such large particles can be obtained for example by emulsifying an aqueous phase containing the plant proteins and at least one alkali metal salt of a carboxylic acid in a hydrophobic phase under conditions compatible with the production of dispersed droplets of appropriate size, especially under conditions of gentle agitation, the addition of a surfactant optionally being omitted. Surprisingly, this gives vesicles visible to the naked eye, whose membrane is elastic and withstands pressure and which remain stable for prolonged periods of time at a temperature of 45° C. in the form of an aqueous suspension.

It has furthermore been discovered that, under given conditions, including the above conditions which give particles, microcapsules or capsules with a mean diameter in excess of 500 µm, the mean diameter of the particles and the proportion of particles with a diameter greater than 1 mm can be increased by incorporating a small amount of an insoluble lipophilic substance into the aqueous phase, into the hydrophobic phase or into both phases before the emulsification is carried out, examples of said substance being titanium oxide, zinc oxide, calcium stearate or an insoluble colorant in the form of a pigment or lake. At the emulsification stage, the insoluble lipophilic substance moves to the oil/water interface and thus stabilizes the large droplets, allowing interfacial crosslinking around these large droplets when the crosslinking agent is subsequently added. A membrane is thus formed to give particles of increased size, in this case particularly capsules and especially microcapsules or capsules with dimensions of the order of a millimeter and possibly even as much as 2 mm or 3 mm.

The particles obtained are perfectly visible to the naked eye and, depending on the nature of the insoluble lipophilic substance used, are in the form of white vesicles or vesicles having the color of the colored substance.

The availability of stable, solid, large and optionally colored particles represents an important technical advance. For example, the fact that the particles are perfectly visible makes it easy to verify the homogeneity of mixtures containing these particles when they are used in the form of a dispersion in various media. It also makes it easier to check the stability of preparations containing said particles.

DETAILED DESCRIPTION OF THE INVENTION

According to a first feature, the present invention covers particles which comprise, at least on the surface, a wall formed of plant proteins crosslinked in particular by means of interfacial crosslinking between the plant proteins and an acylating polyfunctional crosslinking agent comprising at least two acylating groups, covalent bonds being formed between the acylatable groups of the proteins and the acyl groups of the acylating polyfunctional crosslinking agent.

The acylatable groups of the proteins are especially amine groups, hydroxyl groups, thiol groups and carboxylate groups.

Within the framework of the invention, any plant protein can be used, without limitation. Likewise, any polyfunctional crosslinking agent having at least two acylating groups can be used, without limitation.

In one advantageous embodiment of the invention, the above-mentioned plant proteins are extracted especially from leguminous plants, particularly from the following plants: lupin (genus Lupinus), soya (genus Glycine), pea (genus Pisum), chick pea (Cicer), lucerne (Medicago), horse bean (Vicia), lentil (Lens), bean (Phaseolus), colza (Brassica) or sunflower (Helianthus), or else from cereals such as wheat, maize, barley, malt and oats.

In another advantageous embodiment of the invention, the above-mentioned plant proteins are used in the form of pulverulent preparations such as flours, concentrates or isolates, or liquid preparations such as soya milks.

In another advantageous embodiment of the invention, the aqueous solution used to dissolve the plant proteins contained in the pulverulent preparations is an aqueous buffer solution with a pH of between about 4.5 and about 8.

This solution with a pH of between about 4.5 and about 8 is preferably obtained with a salt of a carboxylic acid, particularly an alkali metal or alkaline earth metal salt of a carboxylic acid. It is preferable to use an alkali metal salt of a carboxylic acid, particularly a sodium or potassium salt, preferably a sodium salt, at a concentration of between 0.1% and 20% by weight.

The above-mentioned carboxylic acid can contain a single carboxyl group or several such groups. The carboxylic acids which can be used are especially acetic, oxalic, malonic, succinic, glutaric, dimethylglutaric, adipic, fumaric, maleic, tartaric, malic, citric, lactic and salicylic acids.

In another advantageous embodiment of the invention, the concentration of plant protein in the aqueous phase is between 0.5 and 5% by weight.

In another advantageous embodiment of the invention, the amount of carboxylic acid salt to be added to the liquid plant protein preparations, such as soya milk, is between 0.1% and 20%, preferably between 5 and 15% and particularly preferably about 10% by weight.

In another advantageous embodiment of the invention, the insoluble lipophilic substance to be incorporated into the aqueous phase, into the hydrophobic phase or into both phases in order to increase the particle size is preferably selected from the group comprising insoluble salts of fatty acids and divalent metals, such as calcium or magnesium stearate, talcum, metal oxides such as titanium oxide or zinc oxide, or insoluble colored substances in the form of pigments such as D&C Red 30, or in the form of calcium, aluminum, barium or zirconium lakes of various colorants. This insoluble lipophilic substance can also be present in the bulk of the particles and/or adsorbed on the surface of these particles.

Examples which may be mentioned of insoluble fatty acid salts which can be used are the calcium, magnesium, strontium and barium salts of carboxylic acids with a number of carbons equal to or greater than 12, such as lauric, myristic, palmitic, stearic, oleic and linoleic acids.

The following may be mentioned as examples of lakes which can be used: indigo carmine aluminum lake (blue), Ponceau 4R aluminum lake (red) and Sunset yellow FCF aluminum lake (orange).

In another advantageous embodiment of the invention, the amount of said insoluble lipophilic substance to be incorporated into the aqueous phase, into the hydrophobic phase or into both phases in order to increase the particle size is between 0.01% and 2% by weight of the phase in question.

In another advantageous embodiment of the invention, the above-mentioned acylating polyfunctional crosslinking agent preferably consists of an acid dihalide or an acid dianhydride. The acid dihalide can be selected from the group comprising phthaloyl, terephthaloyl, sebacoyl, glutaryl, adipoyl or succinyl dihalides. It is preferable to use the dichloride of these acids.

According to a second feature, the present invention also covers the use of these particles for the manufacture of a cosmetic or pharmaceutical composition, especially a dermatological composition, or a food composition.

According to a third feature, the present invention also covers a cosmetic or pharmaceutical composition, especially a dermatological composition, or a food composition containing such particles.

In these compositions, the proportion in which the particles of the invention are incorporated may vary within wide limits and will preferably be between 0.01 and 10% by weight, based on the total weight of the final composition.

According to a fourth feature, the present invention also covers a process for the manufacture of the above-mentioned particles with a wall formed of crosslinked plant proteins, said process comprising:

a) the formation of an aqueous solution with a pH of between about 4.5 and about 8 which contains, in solution, at least one plant protein and at least one carboxylic acid salt;

b) the formation of an oily phase;

c) the formation of an emulsion by mixing the above aqueous phase and oily phase, with agitation;

d) the interfacial crosslinking of said plant protein with an acylating polyfunctional crosslinking agent having at least two acylating groups, for a sufficient period of time to obtain particles comprising, at least on the surface, walls formed of plant proteins crosslinked by said crosslinking agent; and e) if desired, the separation of the particles prepared in this way.

In another advantageous embodiment of the process of the invention, the above-mentioned aqueous solution is prepared from pulverulent plant protein preparations using a buffer with a pH of between about 4.5 and about 8 which contains a carboxylic acid salt at a concentration generally of between 0.1 and 20% by weight. The carboxylic acid salts used to manufacture the aqueous buffer solution have been described above.

A currently preferred buffer which may be used is a buffer obtained with a carboxylic acid which is preferably biocompatible and is selected for example from the group comprising an acetate, a succinate and a citrate.

In one advantageous embodiment of the invention, the above-mentioned aqueous solution is obtained from a liquid plant protein preparation by the addition of a carboxylic acid salt at a concentration of between 0.1% and 20% by weight.

In one advantageous embodiment of the invention, the above-mentioned polyfunctional crosslinking agent is selected from an acid dihalide and an acid dianhydride. As indicated above, the dihalide is preferably the dichloride and it will be preferable to use an acid from the list indicated above.

In one advantageous embodiment of the invention, the ratio of the weight of crosslinking agent to the weight of protein used is between 0.03 and 70 parts by weight of crosslinking agent to one part by weight of protein. The interfacial crosslinking reaction is advantageously carried out at a temperature of between 4 and 80° C., preferably of between 15 and 30° C., and at atmospheric pressure.

In one advantageous embodiment of the process of the invention, the oily phase will preferably be formed using either an organic solvent which can easily be removed, such as cyclohexane or a chloroform/cyclohexane mixture, particularly in the ratio 1:4 v/v, or, preferably, a biocompatible oil, particularly a vegetable or mineral oil, or a fatty acid ester or mixture of fatty acid esters, particularly a coconut oil or 2-ethylhexyl cocoate.

In one particular embodiment of the invention, a process will be carried out in an emulsion of the water-in-oil type.

In another embodiment, a process will be carried out in an emulsion of the oil-in-water type.

Within the framework of any one of the processes of the invention, a surfactant, selected from surfactants well known to those skilled in the art, may advantageously be used to facilitate or stabilize the emulsion. Within the framework of the invention, it will be preferable to use a surfactant of the sorbitol ester type, such as the sorbitan trioleate marketed under the tradename Span 85® by ICI.

Moreover, within the framework of the invention, an insoluble additive, such as a pigment, may be used to obtain large particles, particularly capsules, i.e. particles with a size equal to at least about 1 mm or even 2 or 3 mm. Metal oxides such as titanium oxide and zinc oxide, talcum, and insoluble colored substances in the form of pigments or lakes may be mentioned, without implying a limitation, as additives of particular value within the framework of the invention.

Within the framework of the invention, it is thus possible to obtain particles whose dimensions can be adjusted at will from the smallest sizes up to large sizes, i.e. from nanometer sizes up to large sizes greater than 1 mm, in other words capable of ranging up to about 2 mm or even 3 mm. The invention also includes capsules or spheres, i.e. especially nanocapsules or nanospheres and microcapsules or microspheres, in the definition of "particles".

Also, the particles obtained within the framework of the invention, particularly microcapsules, nanocapsules or capsules, can arbitrarily have either aqueous or oily contents and have a satisfactory appearance. They are solid and easy to disperse in a variety of hydrophilic or lipophilic media. The particles according to the invention are stable at 45° C. in the form of an aqueous suspension, whether their contents be aqueous or oily.

In the case of the processes of the invention, it is also possible to incorporate various substances in suspension, for example pigments, in solution, for example a sugar such as glucose, or in emulsion, for example an oil, particularly a paraffin oil.

The particles according to the invention are also biodegradable since they can be lyzed rapidly by an enzyme such as trypsin or any other enzyme well known to those skilled in the art.

Nanoparticles, nanospheres or nanocapsules may be manufactured using the process described in the patent application of the prior art FR-A-2 683 159=WO 93/08908 in the name of the Applicant.

It is seen that the invention affords the production of particles, especially spheres or capsules such as nanospheres or nanocapsules and microspheres or microcapsules, which make it possible to encapsulate substances, particularly active principles, including lipophilic active principles such as vegetable, mineral or synthetic oil, vitamin A and vitamin E derivatives, etc., and hydrophilic active principles such as plant extracts, ascorbic acid, vitamin C PMG, glucose, organic pigments and inorganic pigments. It should be noted that within the description and the claims, "vitamin C PMG" signifies vitamin C magnesium phosphate.

The stability of these particles under different conditions has been observed at temperatures ranging from 4° C. to 90° C. and for pH values ranging from 3 to 11. Thus it has been possible to observe stability lasting more than 6 months at 45° C., in either a dry or a hydrated medium.

The biodegradability of the particles has been demonstrated with the aid of different enzymes, it being possible for these enzymes to be trypsin, chymotrypsin or another protease.

These particles are also perfectly biocompatible and do not cause any skin or eye irritation or have any oral toxicity.

Irrespective of their size, the particles according to the invention can be used in cosmetic compositions for producing emulsion formulations of the water-in-oil or oil-in-water type, hydrophilic gels, hydrophobic gels, shampoos and shower gels.

Thus, as previously stated, these particles or capsules can be used for the preparation of cosmetic or pharmaceutical compositions, especially dermatological compositions, or food compositions by being combined with a variety of active ingredients or excipients well known to those skilled in the art.

Other objects, characteristics and advantages of the invention will become clearly apparent from the following Examples, which are given simply by way of illustration and cannot therefore in any way limit the scope of the invention. The Examples form an integral part of the invention. Thus any characteristic which appears to be novel compared with any state of the art forms an integral part of the invention in its function and its general characteristic. The percentages given in the Examples are by weight, unless indicated otherwise. Moreover, the temperature is room temperature or is expressed in degrees Celsius, unless indicated otherwise. The pressure is atmospheric pressure, unless indicated otherwise.

EXAMPLE 1 OF THE INVENTION

Preparation of microcapsules with a wall formed of crosslinked lupin proteins a) Preparation of the aqueous phase 0.75 g of lupin flour (ultrafine flour of sweet white lupin (CANA) containing 45% of proteins) is dispersed in 15 ml of acetate buffer of pH 7.4. The dispersion is agitated magnetically for 10 min and then centrifuged and the supernatant is separated off.

b) Emulsification 6 ml of the supernatant are dispersed in 30 ml of cyclohexane containing 2% of sorbitan trioleate (Span 85®) by agitation for 5 min at 2000 rpm.

c) Crosslinking 40 ml of a 5% (w/v) solution of terephthaloyl chloride in a chloroform/cyclohexane mixture (1:4 v/v) are added. After agitation for 30 min, the microcapsules are separated off by centrifugation and subsequently washed by resuspension in cyclohexane, then in alcohol to which 2% of polysorbate has been added, then in 95% alcohol and then in water.

This gives a white sediment. Microscopic examination shows attractive solid, transparent, spherical microcapsules which are very slightly spotted, have a distinct and uniform membrane and have a size of between 20 and 50 $\mu$m.

The microcapsules are intact after storage for 5 months in an oven at 45° C. in the form of an aqueous suspension.

EXAMPLE 2 OF THE INVENTION

Microcapsules with a wall formed of crosslinked lupin proteins

The protocol of Example 1 is repeated, the acetate buffer of pH 7.4 being replaced with an acetate buffer of pH 6.8. This again gives a white sediment formed of attractive solid, spherical microcapsules with a size of between 20 and 60 $\mu$m. The microcapsules are intact after storage for 16 weeks in an oven at 45° C. in the form of an aqueous suspension.

EXAMPLE 3 OF THE INVENTION

Microcapsules with a wall formed of crosslinked lupin proteins

The protocol of Example 1 is repeated, the acetate buffer of pH 7.4 being replaced with an acetate buffer of pH 5.9. This again gives a white sediment formed of attractive solid, spherical microcapsules with a size of between 20 and 60 $\mu$m. The microcapsules are intact after storage for 16 weeks in an oven at 45° C. in the form of an aqueous suspension.

EXAMPLE 4 OF THE INVENTION

Microcapsules with a wall formed of crosslinked lupin proteins

The protocol of Example 1 is repeated, the acetate buffer of pH 7.4 being replaced with a succinate buffer of pH 6. This gives attractive solid, spherical microcapsules with a size of between 10 and 50 $\mu$m. The microcapsules are intact after storage for 16 weeks in an oven at 45° C. in the form of an aqueous suspension.

EXAMPLE 5 OF THE INVENTION

Microcapsules with a wall formed of crosslinked lupin proteins

The protocol of Example 1 is repeated, the acetate buffer of pH 7.4 being replaced with a citrate buffer of pH 6. This gives attractive solid, spherical microcapsules with a size of between 20 and 60 $\mu$m. The microcapsules are intact after storage for 15 weeks in an oven at 45° C. in the form of an aqueous suspension.

EXAMPLE 6 OF THE INVENTION

Microcapsules with a wall formed of crosslinked pea proteins

The protocol of Example 1 is repeated, the lupin flour being replaced with a pea protein isolate (containing 90% of proteins: Pisane HD®, COSUCRA). This gives attractive solid, spherical microcapsules with a size of between 20 and 70 $\mu$m. The microcapsules are intact after storage for 4 weeks in an oven at 45° C. in the form of an aqueous suspension.

EXAMPLE 7 OF THE INVENTION

Microcapsules with a wall formed of crosslinked horse bean proteins

The protocol of Example 1 is repeated, the lupin flour being replaced with a horse bean protein concentrate (containing 50% of proteins: Concentrat 50®, Gemef Industrie). This gives attractive solid, spherical microcapsules with a size of between 20 and 60 $\mu$m. The microcapsules are intact after storage for 4 months in an oven at 45° C. in the form of an aqueous suspension.

EXAMPLE 8 OF THE INVENTION

Microcapsules with a wall formed of crosslinked lupin proteins a) Preparation of the aqueous phase 0.75 g of lupin flour (ultrafine flour of sweet white lupin (CANA) containing 45% of proteins) is dispersed in 15 ml of acetate buffer of pH 7.4 which has been heated to a temperature of 35° C. The dispersion is agitated magnetically for 15 min and then centrifuged and the supernatant is separated off.

b) Emulsification 6 ml of the supernatant are dispersed in 30 ml of 2-ethylhexyl cocoate containing 2% of sorbitan trioleate (Span 85®) by agitation for 5 min at 2000 rpm.

c) Crosslinking

The crosslinking is carried out as described in Example 1.

This gives perfectly spherical microcapsules with a size of between 20 and 60 $\mu$m.

They remain stable for more than 14 weeks at a temperature of 45° C. in the form of an aqueous suspension.

Lysis test in trypsin 250 mg of moist microcapsules are introduced into a tube containing 7.5 ml of a 0.4% solution of trypsin (type II-S, from porcine pancreas, Sigma) in a buffer of pH 7.5. The tube is incubated at 37° C. and magnetic agitation is carried out. The lysis is monitored by microscopic examination until the microcapsules have completely disappeared.

Result

The microcapsules have completely disappeared after 20 min.

EXAMPLE 9 OF THE INVENTION

Microcapsules with a wall formed of crosslinked lupin proteins, containing a water-soluble active principle a) Preparation of the aqueous phase 0.75 g of lupin flour (ultrafine flour of sweet white lupin (CANA) containing 45% of proteins) is dispersed in 15 ml of succinate buffer of pH 6 which has been heated to a temperature of 35° C. Magnetic agitation is carried out for 15 min, the dispersion is then centrifuged and the supernatant is separated off. Glucose is dissolved in the supernatant at a concentration of 3%.

The emulsification and crosslinking are then carried out as described in Example 8.

The microcapsules are separated off by centrifugation and then washed several times with ethylhexyl cocoate. This gives perfectly shaped microcapsules with a size of between 20 and 70 μm which contain glucose.

EXAMPLE 10 OF THE INVENTION

Microcapsules with a wall formed of crosslinked pea proteins

The protocol described in Example 8 is repeated, the lupin flour being replaced with a pea protein isolate (containing 90% of proteins: Pisane HD®, Cosucra) and the acetate buffer of pH 7.4 being replaced with a succinate buffer of pH 6.

This gives spherical microcapsules with a size of between 10 and 60 μm which remain stable for more than 8 weeks at a temperature of 45° C. in the form of an aqueous suspension. These microcapsules are lyzed in trypsin in 8 min under the conditions described in Example 8.

EXAMPLE 11 OF THE INVENTION

Microcapsules with a wall formed of crosslinked horse bean proteins

The protocol described in Example 8 is repeated, the lupin flour being replaced with a horse bean protein concentrate (containing 50% of proteins: Concentrat 50®, Gemef Industrie). This gives spherical microcapsules with a size of between 10 and 50 μm which remain stable for more than 8 weeks at a temperature of 45° C. in the form of an aqueous suspension. The microcapsules are lyzed in trypsin in 75 min under the conditions described in Example 8.

EXAMPLE 12 OF THE INVENTION

Large microcapsules of crosslinked horse bean proteins

The protocol described in Example 11 is repeated, the acetate buffer being replaced with a citrate buffer of pH 6, the addition of sorbitan trioleate being omitted and the agitation speed being reduced to 600 rpm. This gives a bulky sediment of opaque capsules visible to the naked eye, which precipitate rapidly.

Size analysis of 300 capsules, carried out under a microscope fitted with a micrometer eyepiece, gives a size range of between 217 and 1643 μm, with a mean diameter of 735 μm, and a proportion of 18% of microcapsules with a size greater than a millimeter.

It is observed that the membrane of the microcapsules is elastic and solid: if pressure is exerted on the microscope observation slide, the diameter of the microcapsules increases while the pressure is being exerted and returns to its initial value when the pressure ceases.

The microcapsules are intact after storage for 7 weeks in an oven at 45° C. in the form of an aqueous suspension.

EXAMPLE 13 OF THE INVENTION

Microcapsules of crosslinked horse bean proteins: increase in size by the addition of titanium oxide to the hydrophobic phase The protocol described in Example 12 is repeated, 0.1% of titanium oxide being dispersed in the oily phase before emulsification. This gives microcapsules with a solid and elastic membrane, which precipitate rapidly.

Size analysis, carried out as in Example 12, gives a size range of 217 to 2170 μm, with a mean diameter of 899 μm, and a proportion of 43% of microcapsules with a size greater than a millimeter.

This Example demonstrates that the addition of titanium oxide to the oily phase affords a substantial increase in the mean diameter of the microcapsules and the proportion of microcapsules with a size greater than a millimeter.

EXAMPLE 14 OF THE INVENTION

Microcapsules of crosslinked lupin proteins: increase in size by the addition of the colorant D&C Red 30 to the aqueous phase The protocol described in Example 8 is repeated, the acetate buffer being replaced with a succinate buffer of pH 6, 0.1% of the pigment D&C Red 30 being dispersed in the aqueous phase, the sorbitan trioleate being omitted and the agitation speed being reduced to 600 rpm. This gives a sediment formed of spherical red vesicles. It is observed that the membrane is elastic and solid: if pressure is exerted on the microscope observation slide, the diameter of the microcapsules increases while the pressure is being exerted and returns to its initial value when the pressure ceases.

The microcapsules are intact after storage for 3 months in an oven at 45° C. in the form of an aqueous suspension. These microcapsules are lyzed by trypsin in 12 min under the conditions described in Example 8.

Size analysis, carried out as in Example 12, gives a size range of 186 to 1240 μm, a mean diameter of 632 μm and a proportion of 6% of microcapsules with a size greater than a millimeter.

A comparative test performed under identical conditions except that the addition of the pigment D&C Red 30 is omitted gives microcapsules of very markedly smaller diameter, with a size range of 150 to 800 μm, a mean diameter of 322 μm and no capsules with a diameter greater than a millimeter.

EXAMPLE 15 OF THE INVENTION

Large microcapsules of crosslinked lupin proteins obtained with the addition of indigo carmine lake to the aqueous phase The protocol described in Example 14 is repeated, the pigment D&C Red 30 being replaced with indigo carmine aluminum lake (Colorcon). This gives blue microcapsules with a solid and elastic membrane. The microcapsules are intact after storage for 5 weeks in an oven at 45° C. in the form of an aqueous suspension.

Size analysis gives a size range of 217 to 1023 μm, a mean diameter of 536 μm and a proportion of 0.3% of microcapsules with a size greater than a millimeter.

EXAMPLE 16

Large microcapsules of crosslinked lupin proteins obtained with the addition of calcium stearate to the aqueous phase The protocol described in Example 14 is repeated, the pigment D&C Red 30 being replaced with calcium stearate. This gives white microcapsules which remain intact after storage for 3 weeks in an oven at 45° C. in the form of an aqueous suspension.

Size analysis gives a size range of 279 to 1240 μm, a mean diameter of 679 μm and a proportion of 7% of microcapsules with a size greater than a millimeter.

EXAMPLE 17 OF THE INVENTION

Large microcapsules of crosslinked lupin proteins obtained with the addition of talcum to the aqueous phase The protocol described in Example 14 is repeated, the pigment D&C Red 30 being replaced with talcum. This gives white microcapsules which remain intact after storage for 7 weeks in an oven at 45° C. in the form of an aqueous suspension.

Size analysis gives a size range of 217 to 1147 µm, a mean diameter of 666 µm and a proportion of 5% of microcapsules with a size greater than a millimeter.

EXAMPLE 18 OF THE INVENTION

Large microcapsules of crosslinked lupin proteins obtained with the addition of titanium oxide to the aqueous phase The protocol described in Example 14 is repeated, the pigment D&C Red 30 being replaced with titanium oxide. This gives white microcapsules. Size analysis, carried out as in Example 12, gives a size range of 248 to 1271 µm, a mean diameter of 620 µm and a proportion of 2% of microcapsules with a size greater than a millimeter.

EXAMPLE 19 OF THE INVENTION

Large microcapsules of crosslinked lupin proteins obtained with the addition of titanium oxide to the hydrophobic phase The protocol described in Example 18 is repeated, the titanium oxide being incorporated not into the aqueous phase but into the hydrophobic phase, said titanium oxide being used at a concentration of 0.05%. This gives white microcapsules. Size analysis gives a size range of 155 to 1674 µm, a mean diameter of 679 µm and a proportion of 17% of microcapsules with a size greater than a millimeter.

EXAMPLE 20

Large microcapsules of crosslinked lupin proteins obtained with the addition of titanium oxide to the hydrophobic phase The protocol described in Example 19 is repeated, the titanium oxide being used at a concentration of 0.1%. This gives white microcapsules. Size analysis gives a size range of 217 to 1860 µm, a mean diameter of 852 µm and a proportion of 37% of microcapsules with a size greater than a millimeter.

EXAMPLE 21 OF THE INVENTION

Large microcapsules of crosslinked lupin proteins obtained with the addition of titanium oxide to the aqueous phase and the hydrophobic phase The protocol described in Example 20 is repeated, the titanium oxide being incorporated into the aqueous phase at a concentration of 0.05% and into the hydrophobic phase at a concentration of 0.05%.

This gives white microcapsules. Size analysis gives a size range of 248 to 1798 µm, a mean diameter of 825 µm and a proportion of 26% of microcapsules with a size greater than a millimeter.

EXAMPLE 22 OF THE INVENTION

Large microcapsules of crosslinked pea proteins obtained with the addition of titanium oxide to the hydrophobic phase The protocol described in Example 10 is repeated, the sorbitan trioleate being omitted, the agitation speed being reduced to 1000 rpm and titanium oxide being incorporated into the hydrophobic phase at a concentration of 0.1%. This gives white microcapsules. Size analysis gives a size range of 124 to 1147 µm, a mean diameter of 565 µm and a proportion of 6% of microcapsules with a size greater than a millimeter.

A comparative test performed under identical conditions except that the addition of titanium oxide is omitted gives microcapsules of very markedly smaller diameter, with a size range of 124 to 868 µm, a mean diameter of 345 µm and no capsules with a diameter greater than a millimeter.

EXAMPLE 23 OF THE INVENTION

Microcapsules of crosslinked lupin proteins with oily contents

Preparation of the aqueous phase 2 g of lupin flour are dispersed in 40 ml of succinate buffer of pH 6 which has been heated to a temperature of 35° C. The dispersion is agitated magnetically for 15 min and then centrifuged and the supernatant is separated off.

Preparation of the oily phase 0.3 ml of sebacoyl chloride is added to 6 ml of fluid paraffin oil.

Emulsification-crosslinking

The oily phase is dispersed in 30 ml of the aqueous phase by agitation at 5000 rpm and the crosslinking reaction is allowed to develop for 60 min. The microcapsules are then washed several times with distilled water.

This gives a supernatant formed of well-shaped, spherical microcapsules with a size of 10–150 µm. All the oil is encapsulated. The microcapsules are intact after storage for 3 months in an oven at 45° C. in the form of an aqueous suspension.

EXAMPLE 24 OF THE INVENTION

Microcapsules of crosslinked horse bean proteins with oily contents

The protocol described in Example 23 is applied, the lupin flour being replaced with the horse bean protein preparation Concentrat 50® and the succinate buffer of pH 6 being replaced with an acetate buffer of pH 7.4. This gives a supernatant formed of well-shaped microcapsules with a size of 30–150 µm. All the oil is encapsulated.

The microcapsules are intact after storage for 2 months in an oven at 45° C. in the form of an aqueous suspension.

EXAMPLE 25 OF THE INVENTION

Microcapsules prepared from soya milk a) Preparation of the aqueous phase 1 g of sodium acetate trihydrate is dissolved in 1 ml of distilled water and this solution is mixed with 10 ml of Bjorg® soya milk (Distriborg).

b) Emulsification 6 ml of aqueous phase are dispersed in 30 ml of cyclohexane containing 2% of sorbitan trioleate by agitation for 5 min at 2000 rpm.

c) Crosslinking 40 ml of a 5% (w/v) solution of terephthaloyl chloride in a chloroform/cyclohexane mixture (1:4 v/v) are added. After agitation for 30 min, the microcapsules are separated off by centrifugation and then washed as described in Example 1.

A substantial creamy white sediment is obtained after centrifugation. Microscopic examination shows attractive spherical microcapsules which have finely spotted contents, a distinct membrane and a size of 10–70 µm. When incubated in an oven at 45° C., the microcapsules are intact after storage for one year in the form of an aqueous suspension and after 8 and a half months in the form of a suspension in a carbopol or xanthan gel, in gelled silicone or groundnut oils or in a gelled lipidic microemulsion.

Toxicological studies were carried out and form the subject of Example 43.

EXAMPLE 26 OF THE INVENTION

Preparation of microcapsules from soya milk

The protocol described in Example 25 is applied, the BJORG soya milk being replaced with CEREAL® soya milk. This gives spherical microcapsules with a size of 10–60 µm which are intact after storage for 5 and a half months in an oven at 45° C. in the form of an aqueous suspension.

EXAMPLE 27 OF THE INVENTION
Preparation of microcapsules from soya milk

The protocol described in Example 25 is applied, the BJORG soya milk being replaced with GAYLORD HAUSER® soya milk. This gives spherical microcapsules with a size of 10–70 μm which are intact after storage for 5 and a half months in an oven at 45° C. in the form of an aqueous suspension.

EXAMPLE 28 OF THE INVENTION
Preparation of microcapsules from soya milk

The protocol described in Example 25 is repeated, the sodium acetate being replaced with sodium citrate dihydrate added at a rate of 0.65 g to 1 ml of water, 0.1% of titanium oxide being dispersed in the aqueous phase, which has been heated to a temperature of 35° C. beforehand, the cyclohexane being replaced with 2-ethylhexyl cocoate, the addition of sorbitan trioleate being omitted and the agitation speed being lowered to 600 rpm.

This gives a bulky white sediment formed of attractive microcapsules with a solid and elastic membrane and with a size of 100 to 900 μm.

EXAMPLE 29 OF THE INVENTION
Microcapsules prepared from soya milk and containing an oil emulsion
a) Preparation of the aqueous phase 2 g of sodium acetate trihydrate are dissolved in 2 ml of distilled water and this solution is mixed with 20 ml of Bjorg® soya milk.
b) First emulsification: oil/water 5 ml of fluid paraffin oil are dispersed in 15 ml of the previous aqueous phase by agitation for 5 min at 5000 rpm.
c) Second emulsification: water/oil 6 ml of the previous emulsion are taken and dispersed in 30 ml of 2-ethylhexyl cocoate containing 1% of sorbitan trioleate by agitation for 5 min at 1200 rpm.
d) Crosslinking 40 ml of a 5% (w/v) solution of terephthaloyl chloride in the cocoate are added. After agitation for 30 min, the microcapsules are separated off by centrifugation and then washed as described in Example 1.

This gives microcapsules with a size of 10–100 μm which contain refringent droplets of paraffin oil.

EXAMPLE 30 OF THE INVENTION
Preparation of microcapsules with oily contents from soya milk
a) Preparation of the aqueous phase 5 g of sodium acetate trihydrate are dissolved in 5 ml of distilled water and this solution is mixed with 50 ml of Bjorg® soya milk.
b) Preparation of the oily phase 0.6 ml of sebacoyl chloride is added to 12 ml of fluid paraffin oil.
c) Emulsification-crosslinking The oily phase is dispersed in the aqueous phase by agitation at 5000 rpm and the crosslinking reaction is allowed to develop for 60 min. The microcapsules are then washed several times with distilled water.

This gives a cream-colored supernatant formed of well-shaped, spherical microcapsules with a size of 100–200 μm. All the oil is encapsulated.

When incubated in an oven at 45° C., the microcapsules are intact after storage for 8 months in the form of an aqueous suspension and after 2 and a half months in the form of a suspension in gelled silicone or groundnut oils.

EXAMPLE 31 OF THE INVENTION
Preparation of nanocapsules with a wall formed of plant proteins a) Manufacture of the plant protein solution required to prepare the nanocapsules 200 g of lupin flour are dispersed in 4 l of succinate buffer of pH 6 which has been heated to a temperature of 35° C. After magnetic agitation for 15 min, the solution is centrifuged and the supernatant is recovered. It is used for the subsequent steps.
b) Preparation of the oily phase 30 ml of sebacoyl chloride are added to 100 ml of fluid paraffin oil. Mixing is carried out at room temperature and the homogeneous solution is used for the subsequent steps.
c) Emulsification/crosslinking The solutions prepared in a) and b) are added continuously and fed into a high pressure homogenizer at a homogenization pressure of between 300 and 1200 bar, for example 800 bar. The nanocapsules obtained have sizes below 1 micron, are remarkably stable and can be used in a large number of cosmetic formulations, including hydrated cosmetic formulations, with no problem of degradation over time. They are visualized as being intact after storage for one month in an oven at 45° C.

EXAMPLE 32 OF THE INVENTION

The 100 ml of fluid paraffin oil used in Example 31-b) can advantageously be replaced with an amount of between 100 and 500 ml of fluid paraffin oil.

EXAMPLE 33 OF THE INVENTION

The 100 ml of fluid paraffin oil used in Example 31-b) can advantageously be replaced with 100 ml of ethyl myristate, 100 ml of isopropyl myristate, 100 ml of ethyl oleate, 100 ml of vitamin E acetate, 100 ml of vitamin A palmitate or 100 ml of benzyl benzoate. Any other oily active ingredient or vegetable oil, or combination thereof, can also be encapsulated in the same way.

EXAMPLE 34 OF THE INVENTION

Phase a) of Example 31 can be replaced with the following preparation: 200 g of horse bean protein concentrate dispersed in 4 l of acetate buffer of pH 7.4. After mixing and gentle heating for 15 min at 35° C., the solution is centrifuged and the supernatant is used in the remainder of the process.

EXAMPLE 35 OF THE INVENTION
Preparation of nanospheres with a wall formed of plant proteins
a) Manufacture of the mixture required for preparing the nanospheres 75 g of lupin flour (ultrafine flour of sweet white lupin (CANA) containing 45% of proteins) are dispersed in 1.5 l of acetate buffer of pH 7.4. After agitation at room temperature for 10 min, the solution is centrifuged and the supernatant is used in the remainder of the process.
b) Preparation of the crosslinking agent 400 g of terephthaloyl chloride are ground in a mortar and added to one liter of CODEX viscous vaseline. The whole is agitated mechanically.
c) Emulsification 6 l of CODEX viscous vaseline oil (viscosity index: 250 centipoises) are introduced into a vat, with agitation, and 320 ml of a surfactant (for example the glycerol sorbitan hydroxyisostearate ARLACEL 780, ICI) are added. The whole is agitated for a few minutes. 1 kg of the solution prepared in a) is then introduced, with agitation, emulsification being carried out in a few minutes at 20,000 rpm with the aid of an Ultra-Turax.

d) Crosslinking

The solution containing the crosslinking agent, prepared in step b), is then introduced into the emulsion and the solid particles present therein are then added as well and will dissolve over time. After agitation for 5 min at 20,000 rpm with the aid of an Ultra-Turax, the solution is agitated mechanically at a reduced speed of rotation for at least 18 h at room temperature. The nanospheres are separated off batchwise by centrifugation and the supernatant is discarded (4000 rpm for 15 min).

e) Washing

The nanospheres are washed successively with an organic phase miscible with the vaseline oil. Examples which may be mentioned are DRAGOXAT® (DRAGOCO), isopropyl myristate (STEARINERIE DUBOIS) and medium chain triglycerides (STEARINERIE DUBOIS). In each wash, 100 ml of nanocapsules are added to 500 ml of organic phase. The whole is agitated for a few minutes and then centrifuged (4000 rpm for 15 min). The nanospheres obtained can be suspended, for example in protein or polysaccharide gels, in an oily phase or in a carboxyvinylic polymer gel (carbomer).

EXAMPLE 36 OF THE INVENTION

Preparation of nanospheres containing a water-soluble or insoluble active principle The procedure is as described in Example 35 except that a number of active principles can be added to the solution manufactured in a), examples being glucose, an amino acid such as glutamine, serine, glycine or cysteine, active principles such as caffeine or theophylline, and plant extracts such as extracts of gingko biloba, Centella asiatica or horse chestnut.

EXAMPLE 37 OF THE INVENTION

The procedure is as described in Example 36 except that the preparation of the phase described in a) is modified as follows:

37-A) Replacement of the acetate buffer of pH 7.4 with an acetate buffer of pH 6.8.

37-B) Replacement of the acetate buffer of pH 7.4 with an acetate buffer of pH 5.9.

37-C) Replacement of the acetate buffer of pH 7.4 with a succinate buffer of pH 6.

37-D) Replacement of the acetate buffer of pH 7.4 with a citrate buffer of pH 6.

37-E) Replacement of the lupin flour with a pea protein isolate.

37-F) Replacement of the lupin flour with a horse bean protein concentrate (containing 50% of proteins: Concentrat 50® from GEMEF INDUSTRIE).

EXAMPLE 38 OF THE INVENTION

Water-in-oil emulsion for cosmetic or pharmaceutical use
Use of the microparticles or nanoparticles in emulsion formulations of the water-in-oil type Formulation 38-A

| | | |
|---|---|---|
| A | Water | qsp 100 |
| | Butylene glycol | 2 |
| | Glycerol | 3 |
| | Sodium dihydroxycetyl phosphate | 2 |
| | Isopropyl hydroxycetyl ether | |
| B | Glycol stearate SE | 14 |
| | Triisononanoin | 5 |
| | Octyl cocoate | 6 |
| C | Butylene glycol | 2 |
| | Methylparaben | |
| | Ethylparaben | |
| | Propylparaben | |
| | pH adjusted to 5.5 | |
| D | Products of the invention | 0.01–10% |

Formulation 38-B

| | | |
|---|---|---|
| A | Water | qsp 100 |
| | Butylene glycol | 2 |
| | Glycerol | 3 |
| | Polyacrylamide | 2.8 |
| | Isoparaffin | |
| | Laureth-7 | |
| B | Butylene glycol | 2 |
| | Methylparaben | |
| | Ethylparaben | |
| | Propylparaben | |
| | Phenoxyethanol | 0.5 |
| | Methylparaben | |
| | Propylparaben | |
| | Butylparaben | |
| | Ethylparaben | |
| | Butylene glycol | 0.5 |
| C | Products of the invention | 0.01–10% |

Formulation 38-C

| | | |
|---|---|---|
| A | Carbomer | 0.50 |
| | Propylene glycol | 3.00 |
| | Glycerol | 5.00 |
| | Water | qsp 100 |
| B | Octyl cocoate | 5.00 |
| | Bisabolol | 0.30 |
| | Dimethicone | 0.30 |
| C | Sodium hydroxide | 1.60 |
| D | Phenoxyethanol | 0.50 |
| | Methylparaben | |
| | Ethylparaben | |
| | Propylparaben | |
| | Butylparaben | |
| | Perfume | 0.3 |
| E | Product of the invention | 0.01–10% |

EXAMPLE 39 OF THE INVENTION

Oil-in-water emulsion for cosmetic or pharmaceutical use
Use of the microparticles and nanoparticles in a formulation of the oil-in-water type

| | | |
|---|---|---|
| A | PEG 30 dipolyhydroxystearate | 3 |
| | Capric triglycerides | 3 |
| | Cetearyl octanoate | 4 |
| | Dibutyl adipate | 3 |
| | Grape seed oil | 1.5 |
| | Jojoba oil | 1.5 |
| | Phenoxyethanol | 0.5 |
| | Methylparaben | |
| | Ethylparaben | |
| | Propylparaben | |
| | Butylparaben | |
| B | Glycerol | 3 |
| | Butylene glycol | 3 |
| | Magnesium sulfate | 0.5 |
| | EDTA | 0.05 |
| | Water | qsp 100 |
| C | Cyclomethicone | 1 |
| | Dimethicone | 1 |
| D | Perfume | 0.3 |
| E | Product of the invention | 0.01–10% |

EXAMPLE 40 OF THE INVENTION

Cosmetic composition
Use of the microparticles and nanoparticles in a formulation of the shampoo or shower gel type

|   |   |   |
|---|---|---|
| A | Xanthan gum | 0.8 |
|   | Water | qsp 100 |
| B | Phenoxyethanol | 0.5 |
|   | Methylparaben |   |
|   | Ethylparaben |   |
|   | Propylparaben |   |
|   | Butylparaben |   |
|   | Butylene glycol | 0.5 |
|   | Methylparaben |   |
|   | Ethylparaben |   |
|   | Propylparaben |   |
| C | Citric acid | 0.8 |
| D | Sodium laureth sulfate | 40.0 |
| E | Product of the invention | 0.01–10% |

EXAMPLE 41 OF THE INVENTION
Cosmetic composition
Use of the microparticles and nanoparticles in a formulation of the lipstick type and other anhydrous products

|   |   |   |
|---|---|---|
| A | Mineral wax | 17.0 |
|   | Isostearyl isostearate | 31.5 |
|   | Propylene glycol dipelargonate | 2.6 |
|   | Propylene glycol isostearate | 1.7 |
|   | PEG 8 beeswax | 3.0 |
|   | Hydrogenated palm kernel oil | 3.4 |
|   | Glycerides, hydrogenated palm glyceride |   |
|   | Lanolin oil | 3.4 |
|   | Sesame oil | 1.7 |
|   | Tribehenin | 1.7 |
|   | Cetyl lactate | 1.7 |
|   | Mineral oil, lanolin alcohol | 3.0 |
| B | Castor oil | qsp 100 |
|   | Titanium dioxide | 3.9 |
|   | CI 15850:1 | 0.616 |
|   | CI 45410:1 | 0.256 |
|   | CI 19140:1 | 0.048 |
|   | CI 77491 | 2.048 |
| C | Product of the invention | 0.01–5 |

EXAMPLE 42 OF THE INVENTION
Cosmetic composition
Use of the microparticles and nanoparticles in an aqueous gel formulation (eye contour gels, slimming gels, etc.)

|   |   |
|---|---|
| Water | qsp 100 |
| Carbomer | 0.5 |
| Butylene glycol | 15 |
| Phenoxyethanol | 0.5 |
| Methylparaben |   |
| Ethylparaben |   |
| Propylparaben |   |
| Butylparaben |   |
| Product of the invention | 0.01–10 |

EXAMPLE 43 OF THE INVENTION
Toxicological studies carried out on the products of Example 25 of the invention
a) Oral toxicity The tests were performed by the protocol consistent with the OECD guideline concerning the study of acute oral toxicity (no. 401 of Feb. 24, 1987), at maximum doses of 5 g/kg body weight, and did not cause any macroscopic lesions attributable to a toxic effect of the product.

The products of the invention (soya microcapsules) obtained in Example 25 are used orally at a dose below 5 g/kg and therefore have zero toxicity.
b) Eye irritation The tests were performed by the official method defined by the decree of May 3, 1990 (Official Journal of the French Republic of Nov. 14, 1990) with the product of the invention (soya microcapsules) and did not cause any lesions of the iris or cornea.

Instilled pure, the products of the invention (soya microcapsules) were found to be non-irritant and the eye tolerance can be considered as very good.
c) Skin irritation The tests were performed by the official method defined by the decree of Feb. 1, 1982 (Official Journal of the French Republic of Feb. 21, 1982) with the product of the invention (soya microcapsules) and did not cause any irritation phenomena.

Applied pure, the products of the invention (soya microcapsules) were found to be non-irritant and the skin tolerance can be considered as excellent.
d) Study of the sensitizing power Maximization tests were performed by a protocol adapted from the method described by MAGNUSSON and KLIGMAN (J. INVEST. DERM. 1969, 52, 268–276).

The products of the invention (soya microcapsules) did not cause any significant macroscopic reaction i. e. any sensitization reaction. They can therefore be considered as hypoallergenic (class I).

What is claimed is:

1. Particles which comprise, at least on the surface, a wall formed of plant proteins crosslinked by means of interfacial crosslinking between the plant proteins having acylatable groups and an acylating polyfunctional crosslinking agent comprising at least two acylating groups, covalent bonds being formed between the acylatable groups of the proteins and the acyl groups of the acylating polyfunctional crosslinking agent.

2. The particles of claim 1 wherein the plant proteins are extracted from leguminous plants.

3. The particles of claim 2 wherein the leguminous plant is selected from the group consisting of: lupin (genus Lupinus), soya (genus Glycine), pea (genus Pisum), chick pea (Cicer), lucerne (Medicago), horse bean (Vicia), lentil (Lens), bean (Phaseolus), colza (Brassica) and sunflower (Helianthus).

4. The particles of claim 1 wherein the plant proteins are extracted from cereals.

5. The particles of claim 4 wherein the cereal is selected from the group consisting of wheat, maize, barley, malt and oats.

6. The particles of claim 1 wherein the plant proteins are used in the form of pulverulent preparations selected from the group consisting of flours, concentrates and isolates, and liquid preparations.

7. The particles of claim 6 wherein said liquid preparations are soya milks.

8. The particles of claim 6 wherein the plant proteins are dissolved at a concentration of between 0.5 and 5% by weight in an aqueous solution with a pH of between about 4.5 and about 8.

9. The particles of claim 8 wherein the aqueous solution of plant protein with a pH of between about 4.5 and about 8 contains at least one carboxylic acid salt at a concentration of between 0.1 and 20% by weight.

10. The particles of claim 9 wherein the carboxylic acid salt is a salt of a metal selected from the group consisting of an alkali metal and an alkaline earth metal, and a carboxylic acid selected from the group consisting of acetic, oxalic, malonic, succinic, glutaric, dimethylglutaric, adipic, fumaric, maleic, tartaric, malic, citric, lactic and salicylic acids.

11. The particles of claim 1 which contain an insoluble lipophilic substance selected from the group consisting of insoluble salts of fatty acids and divalent metals, metal oxides, talcum, and insoluble colored substances.

12. The particles of claim 11 wherein said insoluble salts of fatty acids and divalent metals are selected from the group consisting of calcium stearate and magnesium stearate.

13. The particles of claim 11 wherein said metal oxides are selected from the group consisting of titanium oxide and zinc oxide.

14. The particles of claim 11 wherein said insoluble colored substances are in a form selected from the group consisting of pigments and a colored lake.

15. The particles of claim 14 wherein said colored lake is selected from the group consisting of a calcium lake, an aluminum lake, a barium lake, and a zirconium lake.

16. The particles of claim 11 wherein the insoluble fatty acid salts are selected from the group consisting of calcium, magnesium, strontium and barium salts of carboxylic acids with a number of carbons equal to or greater than 12.

17. The particles of claim 16 wherein said carboxylic acids with a number of carbons equal to or greater than 12 are selected from the group consisting of lauric, myristic, palmitic, stearic, oleic and linoleic acids.

18. The particles of claim 16 wherein the lakes are selected from the group consisting of indigo carmine aluminum lake (blue), Ponceau 4R aluminum lake (red), and Sunset yellow FCF aluminum lake (orange).

19. The particles of claim 1 wherein the acylating polyfunctional crosslinking agent is selected from the group consisting of an acid dihalide and an acid dianhydride.

20. The particles of claim 19 wherein said acid dihalide is selected from the group consisting of phthaloyl, terephthaloyl, sebacoyl, glutaryl, adipoyl and succinyl dihalides.

21. The particles of claim 1 which contain an active principle selected from the group consisting of a cosmetic active principle, a pharmaceutical active principle, and a food active principle.

22. The particles of claim 21 wherein the active principle is selected from the group consisting of a vegetable oil, a mineral oil, a synthetic oil, a vitamin A compound, a vitamin E compound, and a hydrophilic active principle.

23. The particles of claim 22 wherein the hydrophilic active principle is selected from the group consisting of plant extracts, ascorbic acid, vitamin C PMG, glucose, organic pigments, and inorganic pigments.

24. The particles of claim 1 which have a size of between about 10 nanometers and about 3 millimeters.

25. A composition selected from the group consisting of cosmetic composition, a pharmaceutical composition, a dermatological composition, and a food composition, which contains particles of claim 1.

26. A process for the manufacture of particles of crosslinked plant proteins, which comprises:
 a) the formation of an aqueous solution with a pH of between about 4.5 and about 8 which contains, in solution, at least one plant protein and at least one carboxylic acid salt;
 b) the formation of an oily phase;
 c) the formation of an emulsion by mixing the above aqueous phase and oily phase, with agitation;
 d) the interfacial crosslinking of said plant protein with an acylating polyfunctional crosslinking agent having at least two acylating groups, for a sufficient period of time to obtain particles comprising, at least on the surface, walls formed of plant proteins crosslinked by said crosslinking agent; and
 e) if desired, the separation of the particles prepared in this way.

27. The process of claim 26 wherein the concentration of the plant protein in the aqueous phase is between about 0.5 and about 5% by weight.

28. The process of claim 26 wherein the aqueous solution with a pH of between about 4.5 and about 8 contains an amount of carboxylic acid salt which is generally between about 0.1 and 20% by weight.

29. The process of claim 26 wherein the polyfunctional crosslinking agent is selected from the group consisting of an acid dihalide, and an acid dianhydride.

30. The process of claim 26 wherein the ratio of the weight of the polyfunctional crosslinking agent to the weight of plant protein used is generally between 0.03 and 70 parts by weight of crosslinking agent to one part by weight of proteins.

31. The process of claim 26 wherein the oily phase is formed using an organic solvent which can easily be removed selected from the group consisting of cyclohexane, and a chloroform/cyclohexane mixture.

32. The process of claim 26 wherein the oily phase is formed using a biocompatible oil selected from the group consisting of a coconut oil, 2-ethylhexyl cocoate, and a paraffin oil.

33. The process of claim 26 which is a process for performing a water-in-oil emulsion.

34. The process of claim 26 which is a process for performing an oil-in-water emulsion.

35. The process of claim 26 wherein a surfactant of the sorbitan type is used to facilitate or stabilize the emulsion.

36. The process of claim 35 wherein said surfactant of the sorbitan type is sorbitan trioleate.

37. The process of claim 26 wherein, to increase the particle size, an insoluble lipophilic substance is added to the aqueous phase, the hydrophobic phase or both phases, said substance being selected from the group consisting of insoluble salts of fatty acids and divalent metals, talcum, metal oxides, and insoluble colored substances.

38. The process of claim 37 wherein said insoluble colored substances are selected from the group consisting of a pigment, and a lake.

39. The process of claim 37 wherein the insoluble salts of fatty acids and divalent metals are selected from the group consisting of the calcium, magnesium, strontium and barium salts of carboxylic acids with a number of carbons equal to or greater than 12.

40. The process of claim 39 wherein said carboxylic acid with a number of carbons equal to or greater than 12 is selected from the group consisting of lauric, myristic, palmitic, stearic, oleic and linoleic acids.

41. The process of claim 37 wherein said metal oxides are selected from the group consisting of titanium oxide and zinc oxide.

42. The process of claim 37 wherein the insoluble colored substances are selected from the group consisting of organic pigments and lakes.

43. The process of claim 42 wherein said organic pigment is D&C Red 30.

44. The process of claim 42 wherein said lake is selected from the group consisting of a calcium lake, an aluminum lake, a barium lake, and a zirconium lake of colorants.

45. The process of claim 43 wherein said aluminum lake is selected from the group consisting of indigo carmine aluminum lake, which is blue, Ponceau 4R aluminum lake, which is red, and Sunset yellow FCF aluminum lake which is orange.

46. The process of claim 37 wherein the insoluble lipophilic substance is incorporated in an amount of between 0.01% and 2% by weight of the phase in question.

47. The process of claim 26 wherein the interfacial crosslinking reaction is carried out at a temperature of between 4 and 80° C., and at atmospheric pressure.

48. The process of claim 26 wherein the carboxylic acid salt is a salt of a metal selected from the group consisting of an alkali metal and an alkaline earth metal salt of a carboxylic acid selected from the group consisting of acetic, oxalic, malonic, succinic, glutaric, dimethylglutaric, adipic, fumaric, maleic, tartaric, malic, citric, lactic and salicylic acids.

* * * * *